United States Patent [19]

Iversen et al.

[11] Patent Number: 5,456,716
[45] Date of Patent: Oct. 10, 1995

[54] ELASTOMERIC VALVE ASSEMBLY

[75] Inventors: Alfred A. Iversen, Wayzata; Thomas E. Broome, Shakopee; David M. Costello, St. Paul, all of Minn.; Timothy A. Keeter, Swampscott, Mass.

[73] Assignee: PMT Corporation, Chanhassen, Minn.

[21] Appl. No.: 111,592

[22] Filed: Aug. 25, 1993

[51] Int. Cl.⁶ ............................... A61F 2/52; F16K 15/14
[52] U.S. Cl. ............................. 623/8; 137/844; 137/846
[58] Field of Search ............................... 623/8; 137/844, 137/846

[56] References Cited

U.S. PATENT DOCUMENTS

| | | | |
|---|---|---|---|
| 1,041,216 | 10/1912 | Woods | 137/846 |
| 1,702,974 | 5/1928 | MacDonald | 137/846 |
| 4,253,201 | 3/1981 | Ross et al. | 623/8 |
| 4,263,682 | 4/1981 | Bejarano | 623/8 |
| 4,662,883 | 5/1987 | Bell et al. | 623/8 |
| 4,758,198 | 7/1988 | Ishiwa | 137/846 |
| 4,775,379 | 10/1988 | Fogarty et al. | 623/8 |
| 4,917,646 | 4/1990 | Kieves | 137/846 |
| 4,930,535 | 6/1990 | Rinehold | 623/8 |
| 5,019,101 | 5/1991 | Purkait et al. | 623/8 |
| 5,219,360 | 6/1993 | Georgiade | 623/8 |
| 5,248,275 | 9/1993 | McGrath et al. | 137/844 |
| 5,312,363 | 5/1994 | Ryan et al. | 137/846 |

FOREIGN PATENT DOCUMENTS 0469165  7/1990  European Pat. Off. ............ 628/8

OTHER PUBLICATIONS

Silastic Varfill Mammary Implant, Oct. 1977 Dow Corning.

*Primary Examiner*—David H. Willse
*Assistant Examiner*—Bruce E. Snow
*Attorney, Agent, or Firm*—Palmatier, Sjoquist & Helget

[57] ABSTRACT

An elastomeric valve assembly designed for use in an inflatable surgical implant to provide a self sealing means for filling the implant. The valve assembly incorporates vulcanized elastomeric strips molded between two larger silicone sheets, wherein the strips form a collapsible self-sealing channel through which a fill needle may be inserted through slits in the strips and sheets.

15 Claims, 2 Drawing Sheets

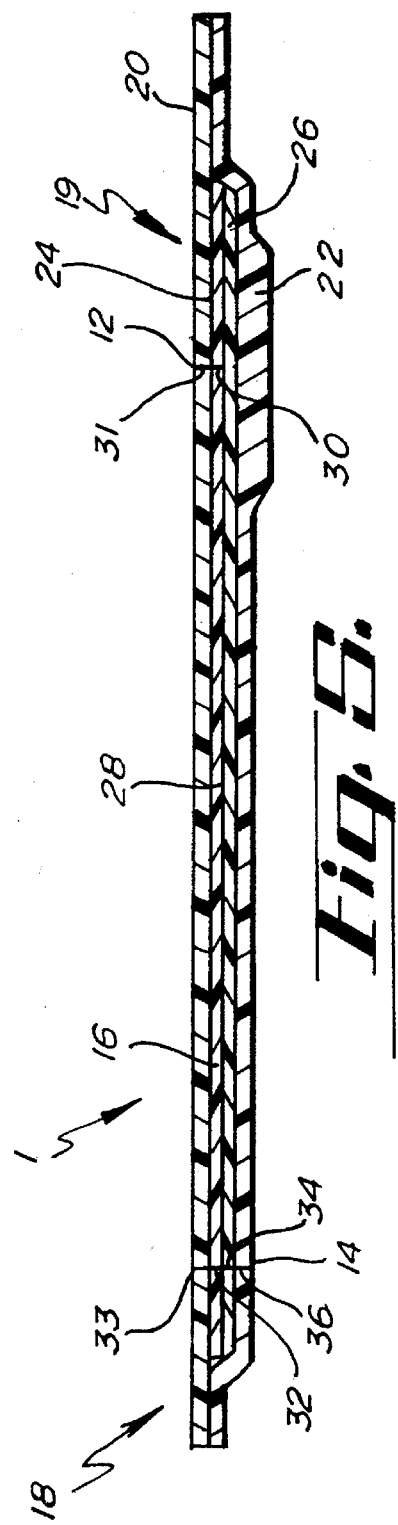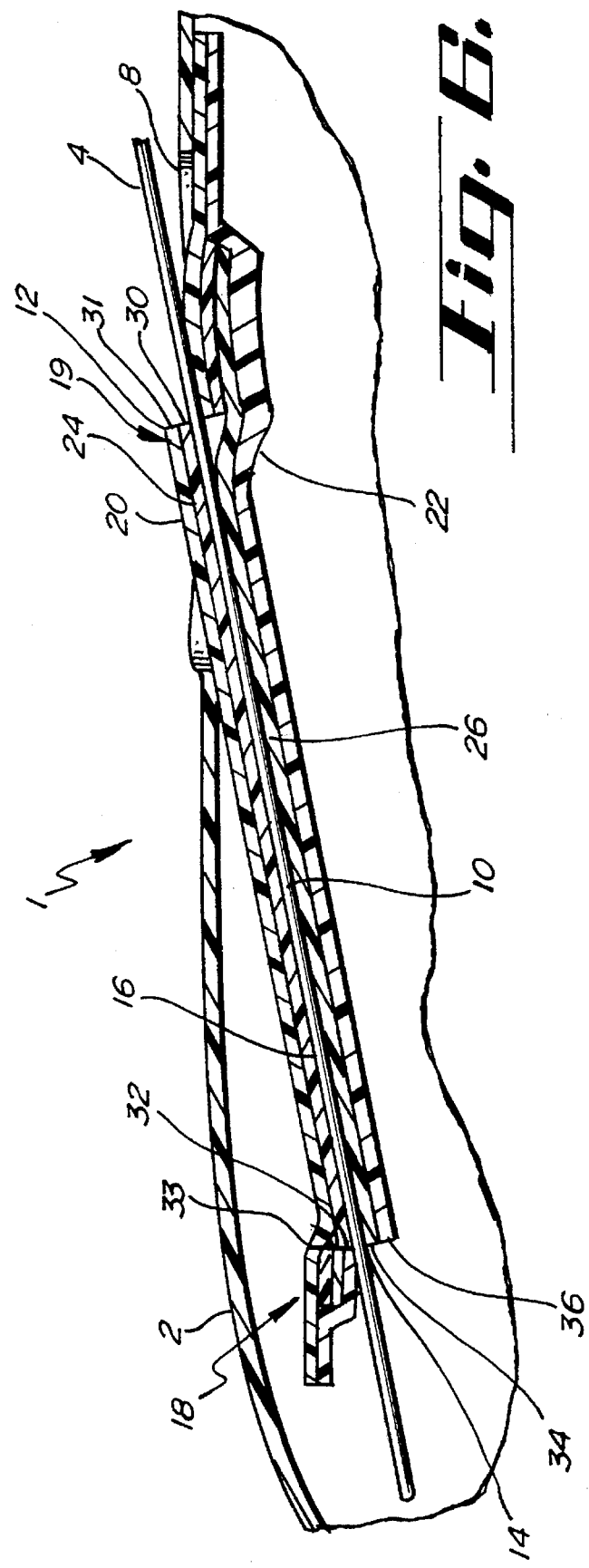

ELASTOMERIC VALVE ASSEMBLY

The present invention relates to an elastomeric valve assembly for use in an implantable device. More narrowly, it is directed to a valve assembly for filling an inflatable implant during surgery, which is self-sealing and prevents leakage of the fill material in subsequent years after implantation.

BACKGROUND OF THE INVENTION

Implantable prosthetic devices, particularly breast implants, are generally known. Most of these devices include a sack-like or envelope-like bladder which is manufactured from an elastomeric material such as silicone rubber and filled with a liquid or gel. The liquid or gel filling can be a silicone fluid or a saline solution. A combination of an elastomeric envelope and liquid or gel fill material is utilized to imitate properties of the tissue being replaced or supplemented.

Envelope-type or bladder-type implants may be pre-filled by the manufacturer or alternatively may be designed to be filled during or after surgery. As recognized by Purkait et al. (U.S. Pat. No. 5,019,101), it has been found to be desirable to utilize implantable devices which are not inflated prior to surgery. This allows the surgeon to determine a proper quantity of fill material or inflation depending upon the available space for tissue expansion or replacement. Further, in some situations, it is desirable to add fluid in stages subsequent to implant. In all applications wherein the device is purchased in a deflated state, it is necessary to include a fill valve assembly which allows addition of fluid or gel to the enclosure created by the bladder or envelope.

A recognized problem in the art when using a fill valve on an implantable prostheses is the potential leakage of the fill material through the valve assembly in the years subsequent to implant and filling. Prior art valves that have been used in such prosthesis, although providing a seal, may not provide an absolute seal, since some leakage can occur. It will be appreciated that although the leakage may be slight, and not noticeable over a short period of time, any decrease in fluid volume in the prosthesis over several years is unacceptable. Leakage has allegedly been tied to certain health problems, but also results in inability of the prosthesis to accomplish the cosmetic results for which it was implanted and filled.

The disclosure of Purkait et al. is directed to solving this recognized problem in the art. The Purkait et al. valve utilizes a main body portion having a channel for receiving a fill tube wherein the main body portion has an unevenly stressed section that includes a selected section of the channel. The unevenly stressed section is stressed so that the selected section of the channel folds back, occluding the channel, when the fill tube is withdrawn. The fill channel is formed by placing a Teflon sheet between two sheets of unvulcanized silicone rubber and heat-pressing the assembly. The Teflon sheet is then removed, leaving a channel between the silicone layers. As recognized by Purkait et al., the channel is not self-sealing, therefore, the sheets must be unevenly stressed to cause folding back in the channel area in order to prevent leakage.

It is believed that the use of a Teflon sheet which is removed from the channel prevents the channel from collapsing to a self-sealing position. That is, a gap will always occur at least at the edge or end of the channel where the Teflon sheet was placed in formation of the valve body. Uneven stressing of the valve body is required to overcome this problem. Further, the removal of a Teflon sheet and pre-stressing complicate the manufacture and assembly of a valve embodying the disclosure of Purkait et al.

Berjarano (U.S. Pat. No. 4,263,682) discloses the use of a release agent between sheets of unvulcanized silicone rubber which are heat-pressed. The only area that does not bond together is the portion that was pre-treated with the release agent. Thus, a channel is created between the sheets of silicone rubber. It is believed that a drawback of this method is that the release agent must be qualified for biocompatibility. Also, in manufacturing such device utilizing a release agent, there is difficulty in controlling the dimensions of the collapsible channel to assure adequate sealing, along with problems associated with gaps created by loss of the release agent, generally a powder. Any gap would reduce the self-sealing capability of the channel.

Accordingly, a need exists for an inflation valve assembly which is self-sealing and readily manufactured. Further, a need exists for a valve assembly which allows tight control of the dimensions of the insertion or fill channel. The insertion channel should be completely collapsible and self-sealing. The present invention addresses these needs as well as other problems associated with existing valve assemblies. The present invention also offers further advantages over the prior art and solves other problems associated therewith.

SUMMARY OF THE INVENTION

The present invention is an elastomeric valve assembly especially useful as an implant inflation valve. The valve assembly is specifically designed to be utilized to fill an inflatable implant during surgery, while preventing leakage from the implant during subsequent years.

The elastomeric valve assembly disclosed herein includes a valve strip or leaf assembly. The valve strip assembly includes a first strip and a second strip of vulcanized elastomeric sheet material. The strips of elastomeric sheet material are coincidentally aligned and in planar contact with one another. The first strip has a slit therethrough proximate one end, while both the first and second strips have registered slits proximate the other end of the valve strip assembly.

The elastomeric valve also includes a valve body which is made from two coincidentally aligned elastomeric sheets having the valve strip assembly located therebetween. The elastomeric sheets making up the valve body have dimensions which are greater than the dimensions of the valve strip assembly, with the excess surface area of the elastomeric sheets extending beyond the perimeter of the valve strip assembly and in planar contact with one another to form a flange-like projection around the perimeter of the valve assembly. The valve body has a slit through one of the elastomeric sheets registered with the one slit in the first strip and a slit on the other end of the elastomeric sheets registered with the other valve strip slit completely through the valve strip assembly.

The elastomeric sheets of the valve body include means for binding the sheets at points of planar contact along the flange-like projections on the perimeter of the valve strip assembly. A collapsible channel is thus formed for inserting a fill needle between the coincidentally aligned first strip and second strip of the valve strip assembly. The means for binding the elastomeric sheets can include use of unvulcanized elastomeric sheets which are heat-pressed to bind one to the other. Alternatively, an adhesive may be utilized to bind the sheets.

The collapsible channel formed between the first and second strips of the valve strip assembly is completely collapsible and self sealing as the strips tack up together. The first and second strip remain an integral part of the valve strip assembly and determine the dimensions of the channel without forming a space or gap which may result in leakage.

Alternatively, the elastomeric implant inflation valve can include an upper strip of vulcanized elastomeric sheet material which has a first end and second end. The upper strip includes a slit therethrough proximate the first end and a slit therethrough proximate the second end. A second strip or lower strip of vulcanized elastomeric sheet material, also having a first end and second end, is placed in coincidental planar contact with the upper strip to form a collapsible channel therebetween. The lower strip has a slit proximate the first end thereof registered with the slit proximate the first end of the upper strip.

The valve body assembly includes an upper valve body which is an elastomeric sheet having a generally circular ingress end and a finger-like projection extending radially from the center of the circular ingress end to define an egress end. The upper valve body overlies the upper strip and includes a first slit therethrough proximate the center of the circular ingress end which is registered with the slit proximate the second end of the upper strip. The upper valve body further includes a slit therethrough proximate the egress end which is registered with the slit proximate the first end of the upper strip.

The valve body assembly also includes a lower valve body which is an elastomeric sheet of like shape to the upper valve body which overlies the lower strip. The lower valve body is in coincidental alignment with the upper valve body and has a slit registered with the slit proximate the first end of the lower strip. The dimensions of the upper and lower valve bodies are greater than the upper and lower strips such that the excess surface area of the valve bodies extends beyond the perimeter of the strips and in planar contact with one another to form a flange-like projection around the implant inflation valve assembly.

The points of ingress and egress define the points of entry and exit for a hemi-tipped fill needle which passes along and through the collapsible channel. The elastomeric material utilized in the construction of the valve has sufficient elasticity to allow passage of a needle through the slits described and through the channel created in the strips of elastomeric material. Upon removal of the needle, the channel completely collapses and seals the valve from leakage as the strips tack up to each other.

In one embodiment of the valve assembly, the first strip and second strip or upper and lower strip of elastomeric material are pigmented with different primary colors so that when the planar faces of the strips are in close proximity with each other, or tacked up to each other, as to seal the interface or channel between the strips, a third color is visible to the surgeon. The third color indicates that the channel has sealed. Preferable materials of construction for all elastomeric materials of the present device are vulcanized and unvulcanized elastomeric sheets of silicone rubber.

In a preferred embodiment, the valve assembly is utilized in an inflatable breast implant. The breast implant includes an elastomeric envelope defining an outer surface of the breast implant and having a hole penetrating the outer surface. The implant inflation valve assembly described above is sealably mounted on the interior surface of the elastomeric envelope to cover the hole, at a position where the slit proximate the second end of the upper strip is accessible through the hole in the elastomeric envelope. Thus, the point of ingress described above is visible through the now sealed hole in the elastomeric envelope of the breast implant. The valve assembly may be sealably mounted within the breast implant by use of an adhesive.

These and various other advantages and features of novelty which characterize the present invention are pointed out with particularity in the claims annexed hereto and forming a part hereof. However, for a better understanding of the invention, its advantages, and the objects obtained by its use, reference is made to the drawings which form a further part hereof, and to the accompanying descriptive matter in which are illustrated and described preferred embodiments of the present invention.

BRIEF DESCRIPTION OF THE DRAWINGS

In the drawings, in which like reference numerals indicate corresponding parts or elements in preferred embodiments of the present invention through the several views:

FIG. 5 is a sectional elevation view taken along line 5—5 of FIG. 2, illustrating the valve in the sealed position; and FIG. 6 is a sectional elevation view taken along line 6—6 of FIG. 1 illustrating the valve assembly with a hemi-tipped fill needle inserted through the collapsible channel.

DETAILED DESCRIPTION OF THE INVENTION

Detailed embodiments of the present invention are disclosed herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one of skill in the art to variously practice the invention.

Figure 1:
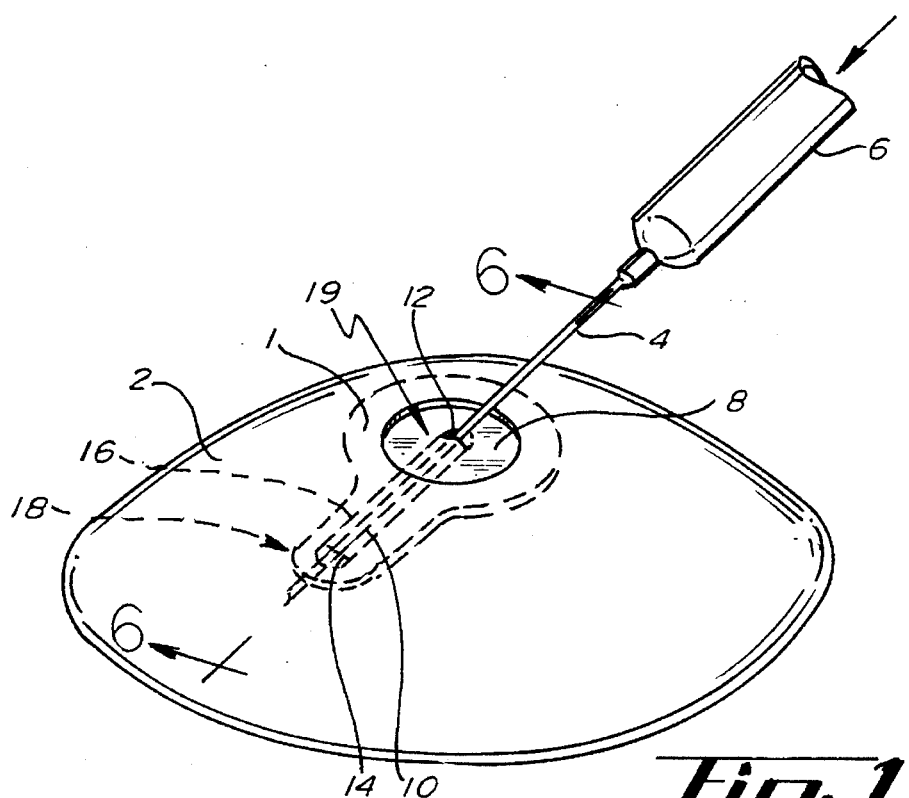
FIG. 1 is a perspective view of an inflatable breast implant of the present invention illustrating the valve assembly sealably mounted.

Referring now to FIG. 1, a perspective view of an inflatable breast implant envelope 2 is illustrated with a valve assembly 1 sealably mounted in a hole 8 in the breast implant envelope 2. As depicted during filling, a syringe 6 with a hemi-tipped fill needle 4 is inserted through a point of ingress 12 in the valve assembly 1 along a collapsible channel 10 and out through a point of egress 14. The breast implant of the present invention would be filled with a fluid such as a saline solution or a silicone gel or fluid during surgery. This feature allows the surgeon to make a determination as to the amount of tissue expansion or replacement which is cosmetically proper.

Figure 2:
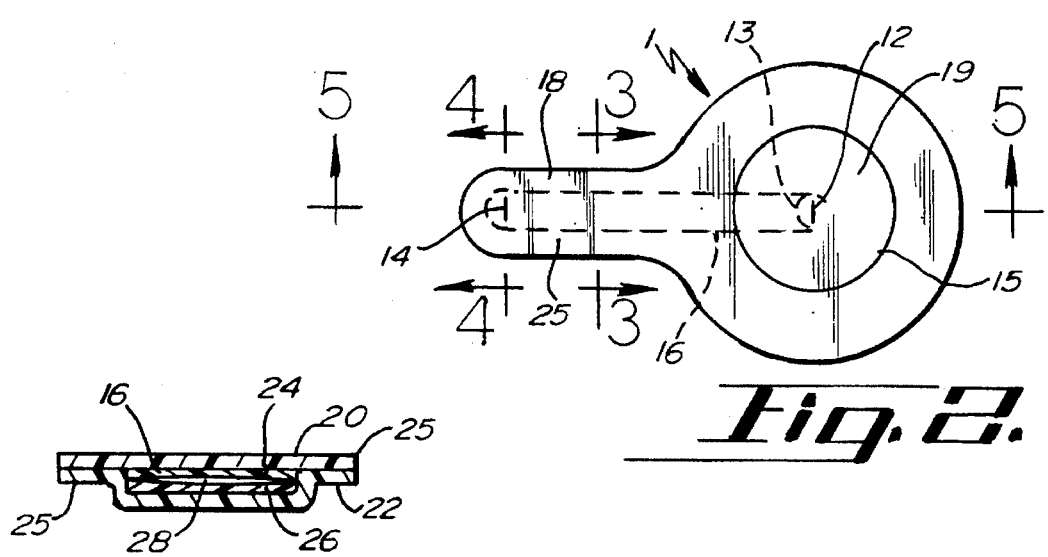
FIG. 2 is a top plan view of the valve assembly.
Figure 3:
FIG. 3 is a sectional elevation view taken along line 3—3 of FIG. 2.
Figure 4:
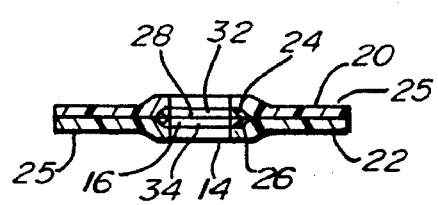
FIG. 4 is a sectional elevation view taken along line 4—4 of FIG. 2, the point of egress.

FIG. 2 shows an embodiment of the valve assembly depicted in FIG. 1, in top plan view. FIG. 2 is best understood in conjunction with the cross-sectional views depicted in FIG. 3 and 4, which are cross-sectional views at lines 3—3 and 4—4 on FIG. 2, respectively. FIG. 2 also shows a central, round, raised portion 15 for flush engagement of the valve 1 with the envelope 2 at hole 8 as to not irritate surrounding tissues.

A valve strip or channel assembly 16 which fixes the dimensions of the collapsible channel 10 is phantom outlined in FIG. 2 and shown in detail in FIGS. 3 through 6. The valve channel assembly 16 includes a first upper strip or piece of vulcanized elastomeric sheet material 24, which is coincidentally aligned and in planar contact with a second lower strip or piece of vulcanized elastomeric sheet material 26. Sheets 24 and 26 may be vulcanized silicone. Together, the first or upper strip 24 and second or lower strip 26 comprise the valve strip assembly 16 forming a channel 10 therebetween. A silicone based lubricant (365 Dow Corning) may optionally be applied to the strips 24 and 26 within channel 10 to encourage the strips 24 and 26 to tack up and close channel 10.

The upper strip of vulcanized elastomeric sheet material 24 has first end 18 and a second end 19 including a slit 32 therethrough proximate the first end 18 and a slit 30 therethrough proximate the second end 19.

The second strip of elastomeric material or lower strip of elastomeric sheet material 26 also has a first end 18 and a second end 19 in coincidental planar contact with the upper strip 24 and forming a collapsible channel 10 therebetween. The lower strip 26 has a slit 34 proximate the first end 18 which is registered with the slit 32 proximate the first end 18 of the upper strip 24.

The valve assembly 1 includes two coincidentally aligned elastomeric sheets 20, 22 or, alternatively, an upper valve body 20 and a lower body 22. The valve body has the valve channel or strip assembly 16 located between the upper sheet 20 and lower sheet 22. As depicted in FIG. 2, the dimensions of the elastomeric sheets which suitably may be silicone which make up the valve body, 20, 22 are greater than the dimensions of the valve strip assembly 16 such that the excess surface area of the elastomeric sheets extends beyond the perimeter of the valve strip assembly 16 in planar contact with one another to form a flange-like projection 25 around the perimeter of the valve assembly 1.

The valve body 20, 22 has a slit 12 through one of the elastomeric sheets registered with one of the slits 30 in the valve strip assembly 16 and a slit 14 on the other of the elastomeric sheets registered with the upper and lower slits 32 and 33 on the valve strip or channel assembly 16.

In a preferred embodiment, the upper valve body 20 includes an elastomeric sheet having a generally circular ingress end 19 and a finger-like projection extending radially from the center of said circular ingress end to define an egress end 18. The upper valve body 20 overlies the upper strip 24. The upper valve body 20 has a slit 31 therethrough proximate the center of the circular ingress end 19 registered with the slit 30 proximate the second end 19 of the upper strip 24. The upper valve body 20 further includes a slit 33 therethrough proximate the egress end 18 registered with the slit 32 proximate the first end 18 of the upper strip 24.

The above preferred embodiment also includes a lower valve body 22 which is made from an elastomeric sheet of like shape to the upper valve body 20 and in coincidental alignment with the upper valve body 20. The lower valve body 22 has a slit 36 therethrough registered with the slit 34 proximate the first end 19 of the lower strip 26. Again, the dimensions of the upper 20 and lower 22 valve bodies are greater than the upper 24 and lower 26 strips such that the excess surface area of the valve bodies 20, 22 extend beyond the perimeter of the strips 24, 26 in planar contact with one another to form a flange-like projection 25 around the implant inflation valve assembly 1. The point of ingress 12 and point of egress 14 define the points of entry and exit for a fill needle 4 which passes through the collapsible channel 10.

Means for binding the elastomeric sheets of the valve body, the upper valve body 20 and lower valve body 22, at points of planar contact on the flange-like projection 25 around the perimeter of the valve strip assembly, are included in the valve assembly 1 of the present invention. The means for binding the elastomeric sheets can include use of an adhesive, however, it is preferable to utilize unvulcanized sheet material for the valve body parts 20 and 22 in contrast to the vulcanized material use for the valve strips 24 and 26, and subsequently heat-pressing the assembly 1, wherein the points of planar contact on the upper valve body 20 and lower valve body 22 will adhere to one another while the space or channel 10 between the points of planar contact of the upper strip 24 and lower strip 26 will not adhere due to pre-vulcanization. Whether vulcanized or unvulcanized, the preferred elastomeric materials utilized in the valve assembly 1 are sheets of silicone rubber. If an adhesive is utilized, room temperature vulcanizing (RTV) silicone adhesives can be used.

As illustrated in the figures, the layers of the various sheet materials 20 and 22 utilized in manufacturing devices of the present device are indicated by distinct lines. However, it is recognized that when the parts are heat-pressed to adhere the unvulcanized sheets 20 and 22, the valve body becomes vulcanized and completely surrounds and adheres to the pre-vulcanized strips. Further, after heat-pressing the assembly, the upper and lower valve bodies 20, 22 bond during vulcanization. Thus, when the unvulcanized sheets are pressed together, the materials flow together and actually join so that no seam is visible between the upper and lower valve bodies 20 and 22. The figures depict the various layers in a pre-heat-pressed state so that it is evident the way in which the layers cooperate to form the assembly prior to heat pressing.

In one embodiment of the valve assembly 1, the upper strip 24 and lower strip 26 of the valve strip assembly are pigmented with different primary colors so that when planar faces of the strips 24, 26 are in close proximity to one another to seal the collapsible channel 10, a third color is visible. This would benefit the surgeon filling the breast implant 2 by indicating whether or not there is any problem with the sealing of the channel 10.

FIG. 5 illustrates a cross-sectional view of the valve assembly 1 along line 5—5 of FIG. 2. This drawing shows the valve assembly 1 in a sealed position prior to or subsequent to filling the implant.

FIG. 6 depicts the valve assembly 1 in a cross-sectional view along line 6—6 of FIG. 1 wherein the valve assembly 1 is illustrated with a hemi-tipped fill needle 4 inserted in the collapsible channel 10 of the valve assembly 1. The special tip design will help to prevent punctures in the valve channel 10 during insertion. The needle 4 may also be coated with Teflon® or other suitable material to facilitate needle 4 insertion into the channel 10 of valve 1.

Together, FIGS. 5 and 6 show the relative relationship of slits 12 (comprised of slits 30 and 31) and 14 (comprised of slits 32, 33, 34 and 36) and elastomeric layers described above in cooperation with one another to make an operable assembly.

In forming slit 12, a small disc 13 may be placed between strips 24 and 26 at the second end 19 to protect the lower strip 26 and valve body 22 from puncture when cutting to form strip 14. Afterwhich, disc 13 may be removed through slit 12. Slit 14 may simply be formed by puncturing valve bodies 20 and 22 and strips 24 and 26 at slit 14.

The upper strip 24 includes the slit 30 proximate the second end 19. The upper strip 24 also includes the slit 32 proximate the first end 18. The lower strip 26 includes the slit 34 proximate the first end 18 registered with the slit 32 proximate the first end 18 of the upper strip 24.

The upper valve body 20 has a first slit 31 at the point of ingress 12. The first slit 31 is registered with the slit 30 proximate the second end 19 of the upper strip 24. The upper valve body 24 also includes a second slit 33 proximate the point of egress 14 and registered with the slit 32 proximate the first end 18 of the upper strip 24. The lower valve body 22 has a slit 36 registered with the slit 34 proximate the first end 18 of the lower strip 26.

FIG. 6 clearly illustrates how the above-described slits 30, 31 (collectively 12) and 32, 33, 34 and 36 (collectively 14) cooperate with one another when passing the fill needle 4 through the collapsible channel 10 of the valve assembly 1. FIG. 6 also shows the relative location of the valve assembly 1 within a breast implant envelope 2. The fill needle 4 enters the valve assembly 1 at the point of ingress 12, passing through slits 30 and 31 to enter the channel 10. The needle 4 exits the valve assembly 1 at the point of egress 14 through registered slits 34 and 36. Alternatively, the needle 4 could exit the valve assembly 1 at registered slits 32 and 33.

New characteristics and advantages of the invention covered by this document have been set forth in the foregoing description. It will be understood, however, that this disclosure is, in many respects, only illustrative. Changes may be made in details, particularly in matters of shape, size, and arrangement of parts, without exceeding the scope of the invention. The scope of the invention is, of course, defined in the language in which the appended claims are expressed.

What is claimed is:

1. An elastomeric valve assembly comprising:
   (a) a valve channel assembly including two opposing vulcanized elastomeric elongate pieces in planar contact with each other forming a collapsed openable channel therebetween having a first end and a second end, the pieces of the valve channel assembly being pigmented with different primary colors so that when said pieces are in close contact with each other to seal the channel, a third color is visible; and
   (b) a valve body of vulcanized elastomer material entirely surrounding the valve channel assembly having a first opening in communication with the first end of the channel and a second opening in communication with the second end of the channel.

2. An elastomeric valve assembly comprising:
   (a) a valve strip assembly including a first strip of vulcanized elastomeric sheet material coincidentally aligned and in planar contact with a second strip of vulcanized elastomeric sheet material each having opposing ends, said first strip having a first slit therethrough proximate one end and said first and second strips having registered second and third slits therethrough proximate the other end;
   (b) a valve body including two coincidentally aligned elastomeric sheets, having said valve strip assembly located therebetween, wherein the dimensions of said elastomeric sheets are greater than the dimensions of said valve strip assembly forming a flange-like projection around the perimeter of the valve assembly, said valve body further having a first slit through one of said elastomeric sheets registered with said first slit in said valve strip assembly and second and third slits on the elastomeric sheets registered with the second and third slits on said valve strip assembly; and
   (c) means for binding the elastomeric sheets of said valve body at points of planar contact on said flange-like projections around the valve strip assembly wherein a collapsible channel for inserting a fill needle is formed between said coincidentally aligned first strip and second strip.

3. The valve assembly of claim 2, wherein said first strip and said second strip are pigmented with different primary colors so that, when said strips are in close proximity with each other to seal the channel, a third color is visible.

4. The valve assembly of claim 2, wherein the means for binding the elastomeric sheets of said valve body includes utilizing unvulcanized elastomer sheets which are heat pressed upon assembly to form the valve body assembly.

5. The valve assembly of claim 2, wherein the means for binding the elastomeric sheets of said valve body is a room temperature vulcanizing silicone adhesive.

6. The valve assembly of claim 2, wherein the valve assembly is manufactured from sheets of silicone rubber.

7. The valve assembly of claim 2, further comprising a hemi-tipped fill needle for insertion in the first opening, along the channel and out the second opening.

8. The valve assembly of claim 7, wherein the needle is teflon coated.

9. An elastomeric implant inflation valve assembly comprising:
   (a) an upper strip of vulcanized elastomeric sheet material having a first end and a second end, said upper strip including a slit therethrough proximate said first end and a slit therethrough proximate said second end;
   (b) a lower strip of vulcanized elastomeric sheet material having a first end and a second end in coincidental planar contact with said upper strip and forming a collapsible channel therebetween, said lower strip having a slit proximate said first end thereof registered with said slit proximate said first end of said upper strip;
   (c) an upper valve body including an elastomeric sheet having a generally circular ingress end and a finger-like projection extending radially from the center of said circular ingress end to define an egress end, said upper valve body overlying said upper strip, said upper valve body having a first slit therethrough proximate the center of said circular ingress end registered with the slit proximate the second end of said upper strip, said upper valve body further including a slit therethrough proximate said egress end registered with said slit proximate said first end of said upper strip;
   (d) a lower valve body including an elastomeric sheet of like shape to said upper valve body overlying said lower strip, said lower valve body in coincidental alignment with said upper valve body and having a slit therethrough registered with said slit proximate said first end of said lower strip, said upper and lower valve bodies forming a flange-like projection around the upper and lower strips wherein the slits define the points of entry and exit for a fill needle which passes along said collapsible channel; and
   (e) means for binding the upper and lower valve body at said flange-like projection.

10. The valve assembly of claim 9, wherein the means for binding the upper and lower valve bodies at points of planar contact includes utilizing unvulcanized elastomeric sheets which are heat pressed upon assembly to form the elastomeric implant valve assembly.

11. The valve assembly of claim 10, wherein the elastomeric implant inflation valve assembly is manufactured from sheets of silicone rubber.

12. An inflatable breast implant comprising:
 (a) an elastomeric envelope defining an outer surface of said breast implant having a hole penetrating said outer surface;
 (b) an implant inflation valve assembly which includes,
  (i) an upper strip of vulcanized elastomeric sheet material having a first end and a second end, said upper strip including a slit therethrough proximate said first end and a slit therethrough proximate said second end,
  (ii) a lower strip of vulcanized elastomeric sheet material having a first end and a second end in coincidental planar contact with said upper strip, and forming a collapsible channel therebetween having a slit proximate said first end thereof registered with said slit proximate said first end of said upper strip,
  (iii) an upper valve body including an elastomeric sheet having a generally circular ingress end and a finger-like projection extending radially from the center of said circular ingress end to define an egress end, said upper valve body overlying said upper strip, said upper valve body having a first slit therethrough proximate the center of said circular ingress end registered with the slit proximate the second end of said upper strip, said upper valve body further including a slit therethrough proximate said first end registered with said slit proximate said first end of said upper strip,
  (iv) a lower valve body including an elastomeric sheet of like shape to said upper valve body overlying said lower strip, in coincidental alignment with said upper valve body and having a slit therethrough registered with said slit proximate said first end of said lower strip, wherein dimensions of said upper and lower valve body are greater than dimensions of said upper and lower strips such that the excess surface area of the valve bodies extends beyond the perimeter of said strips in planar contact with one another to form a flange-like projection around the implant inflation assembly, and
  (v) means for binding the upper and lower valve bodies at points of planar contact on said flange-like projection; and
 (c) means for sealably mounting said inflation valve assembly on said elastomeric envelope to cover said hole at a position wherein said slit proximate the second end of said upper strip is accessible through said hole in said elastomeric envelope.

13. The breast implant of claim 12, wherein the means for binding the upper and lower valve bodies at points of planar contact including utilizing unvulcanized elastomer sheets which are heat pressed upon assembly to form the implant inflation valve assembly.

14. The breast implant of claim 12, wherein said means for sealably mounting said inflation valve assembly is an adhesive.

15. The breast implant of claim 14, wherein the adhesive is a room temperature vulcanizing silicone adhesive.

* * * * *